US011495336B2

(12) United States Patent
Piron et al.

(10) Patent No.: US 11,495,336 B2
(45) Date of Patent: Nov. 8, 2022

(54) SYSTEM AND METHOD FOR DETERMINING HEALTH CARE PROCEDURES AND REIMBURSEMENT

(71) Applicant: SYNAPTIVE MEDICAL INC., Toronto (CA)

(72) Inventors: Cameron Anthony Piron, Toronto (CA); Arun Victor Jagga, Mississauga (CA); Murugathas Yuwaraj, Markham (CA); Thanh Vinh Vuong, Kitchener (CA)

(73) Assignee: Synaptive Medical Inc., Toronto (CA)

( * ) Notice: Subject to any disclaimer, the term of this patent is extended or adjusted under 35 U.S.C. 154(b) by 344 days.

(21) Appl. No.: 16/323,805

(22) PCT Filed: Aug. 18, 2016

(86) PCT No.: PCT/IB2016/054960
§ 371 (c)(1),
(2) Date: Feb. 7, 2019

(87) PCT Pub. No.: WO2018/033778
PCT Pub. Date: Feb. 22, 2018

(65) Prior Publication Data
US 2019/0172572 A1 Jun. 6, 2019

(51) Int. Cl.
*G16H 10/60* (2018.01)
*G16H 30/40* (2018.01)
(Continued)

(52) U.S. Cl.
CPC ............. *G16H 10/60* (2018.01); *G06F 21/45* (2013.01); *G06F 21/6254* (2013.01);
(Continued)

(58) Field of Classification Search
CPC ........ G06H 10/60; G16H 30/40; G06F 21/45; G06F 21/6254; G06F 19/322; G06F 19/328; G06Q 50/22
(Continued)

(56) References Cited

U.S. PATENT DOCUMENTS

| 2012/0033871 A1* | 2/2012 | Vining | ................. G06T 7/0012 |
| | | | 382/132 |
| 2012/0173266 A1* | 7/2012 | Brush | .................... G16H 50/30 |
| | | | 705/2 |

(Continued)

FOREIGN PATENT DOCUMENTS

| WO | WO-2015162037 A1 * | 10/2015 | ......... G06Q 10/0633 |
| WO | 2016019465 A1 | 2/2016 | |
| WO | WO-2016019465 A1 * | 2/2016 | ......... G06F 21/6245 |

OTHER PUBLICATIONS

James N. Weinstein, DO, MSc; Tor D. Tosteson, ScD; Jon D. Lurie, MD, MS; et al, "Surgical vs Nonoperative Treatment for Lumbar Disk Herniation The Spine Patient Outcomes Research Trial (SPORT): A Randomized Trial", JAMA. 2006;296(20):2441-2450 (Year : 2006).*

*Primary Examiner* — Joshua B Blanchette

(57) ABSTRACT

A method and system is provided for recording a health care event, optimizing medical procedures and calculating reimbursement. The method includes: acquiring metadata comprising a patient identifier, a practitioner identifier, a health care site identifier, an entry time and a medical reason for the health care event; receiving a reimbursement request; generating a procedures list based on the medical reason; selecting a procedure; generating a list of required data types and a list of required quality data for the procedure; acquiring raw data comprising the procedure, a medical device identifier, an entry time and one or more quality data from the medical device for the procedure; and calculating a
(Continued)

reimbursement for the health care event based on the procedure, the medical device identifier, the required quality data and the quality data from the medical device. The method implements iterative learning using the collected data to determine optimal health care procedures.

13 Claims, 7 Drawing Sheets

(51) Int. Cl.
    *G16H 30/20*             (2018.01)
    *G06Q 30/04*             (2012.01)
    *G06F 21/45*             (2013.01)
    *G06F 21/62*             (2013.01)

(52) U.S. Cl.
    CPC ............. *G06Q 30/04* (2013.01); *G16H 30/20* (2018.01); *G16H 30/40* (2018.01)

(58) Field of Classification Search
    USPC .......................................................... 705/2, 3
    See application file for complete search history.

(56) References Cited

U.S. PATENT DOCUMENTS

| | | | |
|---|---|---|---|
| 2013/0317848 A1* | 11/2013 | Savin ..................... | G16H 10/60 705/3 |
| 2014/0149133 A1* | 5/2014 | Gibby ................ | G06Q 10/0639 705/2 |
| 2015/0031081 A1 | 1/2015 | Vervecken et al. | |
| 2015/0310181 A1* | 10/2015 | Schroeder ............. | G16H 15/00 705/2 |
| 2016/0042483 A1* | 2/2016 | Vo .......................... | G16H 10/60 705/3 |

\* cited by examiner

| Procedure: Resection | Time used | Number of items used | Data Quality | Devices | Tools | Time used |
|---|---|---|---|---|---|---|
| Resection with Device A | 54 min | 2 | Speed every 5s | 54 min | | |
| Navigation with Device B | 36 min | 1 | | 36 min | | |
| ECOG sensors | n/a | 6 | | n/a | | |
| Imaging feed NFOV | n/a | | 1080p | n/a | | |
| Prescan A | n/a | 1 | Slice thickness = 2mm | n/a | | |
| Prescan B | 46 min | 1 | Slice thickness = 4mm | 46 min | | |
| Intraop scan A | 1:34 min | 1 | | 1:34 min | | |
| Postscan A | n/a | 2 | | n/a | | |

FIGURE 7

SYSTEM AND METHOD FOR DETERMINING HEALTH CARE PROCEDURES AND REIMBURSEMENT

CROSS REFERENCES TO RELEATED APPLICATIONS

This application is a national stage entry of international patent application no. PCT/IB2016/054960 filed on Aug. 18, 2016.

TECHNICAL FIELD

The present disclosure relates to health care data and more specifically to verified health care data for improved patient care and reimbursement calculation.

BACKGROUND

In the health care industry, services and products are often provided to a beneficiary by a health care provider and the health care provider is subsequently reimbursed by a third party. This reimbursement by a third party, the "payer", to a health care provider is typically based on a benefit claim initiated by the health care provider.

The processes for claim submission and reimbursement typically focus on the billing codes that summarize the care provided and largely ignore the clinical data and information related to the care provided. Thus, the processes do not account for the condition of the patient, the quality of the care provided or the appropriateness of the care provided, given the particular clinical circumstances surrounding the patient and the encounter. As such, the standards of review for reimbursement are based on generalities rather than the provision of appropriate and effective high quality care. These problems are compounded since the information technology systems for providing care do not interact with the systems for reimbursement. As a result, the cost of providing care and the administration of care is unreasonably high.

There is a need for a system and methods to include medically supported quality data in the process of providing and paying for care, to improve the level of care and allow providers to employ the best medicine while receiving the appropriate level of reimbursement for the care provided.

SUMMARY

An object of the present invention is to provide methods and systems for determining optimal health care procedures and for calculating reimbursement for health care events.

Thus by one broad aspect of the present invention, a computer-implemented method for recording a health care event and calculating a reimbursement is provided, the method comprising: acquiring metadata for the health care event, the metadata comprising a patient identifier, a patient identifier entry time, a practitioner identifier, a practitioner identifier entry time, a health care site identifier, a health care site identifier entry time and a medical reason for the health care event; receiving a request for reimbursement; generating a list of a priori agreed upon procedures based on the medical reason; selecting a procedure from the list of procedures; generating a list of required perioperative data types associated with the care (including the procedure); generating a list of required quality metrics for the procedure; acquiring raw data for the health care event, the raw data comprising the procedure, a medical device identifier, a medical device identifier entry time and one or more quality data from the medical device for the procedure; and calculating a reimbursement for the health care event based on at least the procedure, the medical device identifier, the required quality data and the one or more quality data from the medical device.

By another broad aspect of the present invention, a computer-implemented method for recording a health care event and calculating a reimbursement is provided, the method comprising: acquiring metadata for the health care event, the metadata comprising a patient identifier, a patient identifier entry time, a practitioner identifier, a practitioner identifier entry time, a health care site identifier, a health care site identifier entry time and a medical reason for the health care event; receiving a request for reimbursement; generating a list of procedures based on the medical reason; generating a list of required data types and a list of required quality data for each of the procedures; acquiring raw data for the health care event, the raw data comprising a procedure selected from the list of procedures, a medical device identifier for a medical device used in the procedure, a medical device identifier entry time and one ore more quality data from the medical device used in the procedure; and calculating a reimbursement for the health care event based on at least the procedure the medical device identifier, the list of required quality data and the one ore more quality data from the medical device.

By another broad aspect of the present invention, a system to determine a reimbursement for a health care event is provided, the system comprising: a database for storing metadata for the health care event, the metadata comprising a patient identifier, a practitioner identifier, a health care site identifier, a time entry for each of the patient identifier, the practitioner identifier and the health care site identifier, and a medical reason for the health care event; a database for storing raw data for the health care event, the raw data including a list of procedures for the medical reason, a procedure selected from the list of procedures, a list of data types for the procedure, a list of quality data for the procedure, a medical device identifier, a time entry for the medical device identifier, and at least one quality data from the list of quality data, measured from the medical device for the health care event; a processor in communication with the metadata database and the raw data database; and a memory with an executable application for calculating the reimbursement quantum for the health care event based on at least the procedure, the medical device and the quality data.

A further understanding of the functional and advantageous aspects of the disclosure can be realized by reference to the following detailed description and drawings.

BRIEF DESCRIPTION OF THE DRAWINGS

FIG. 7 illustrates an example data requirements checklist.

DETAILED DESCRIPTION

Figure 1:
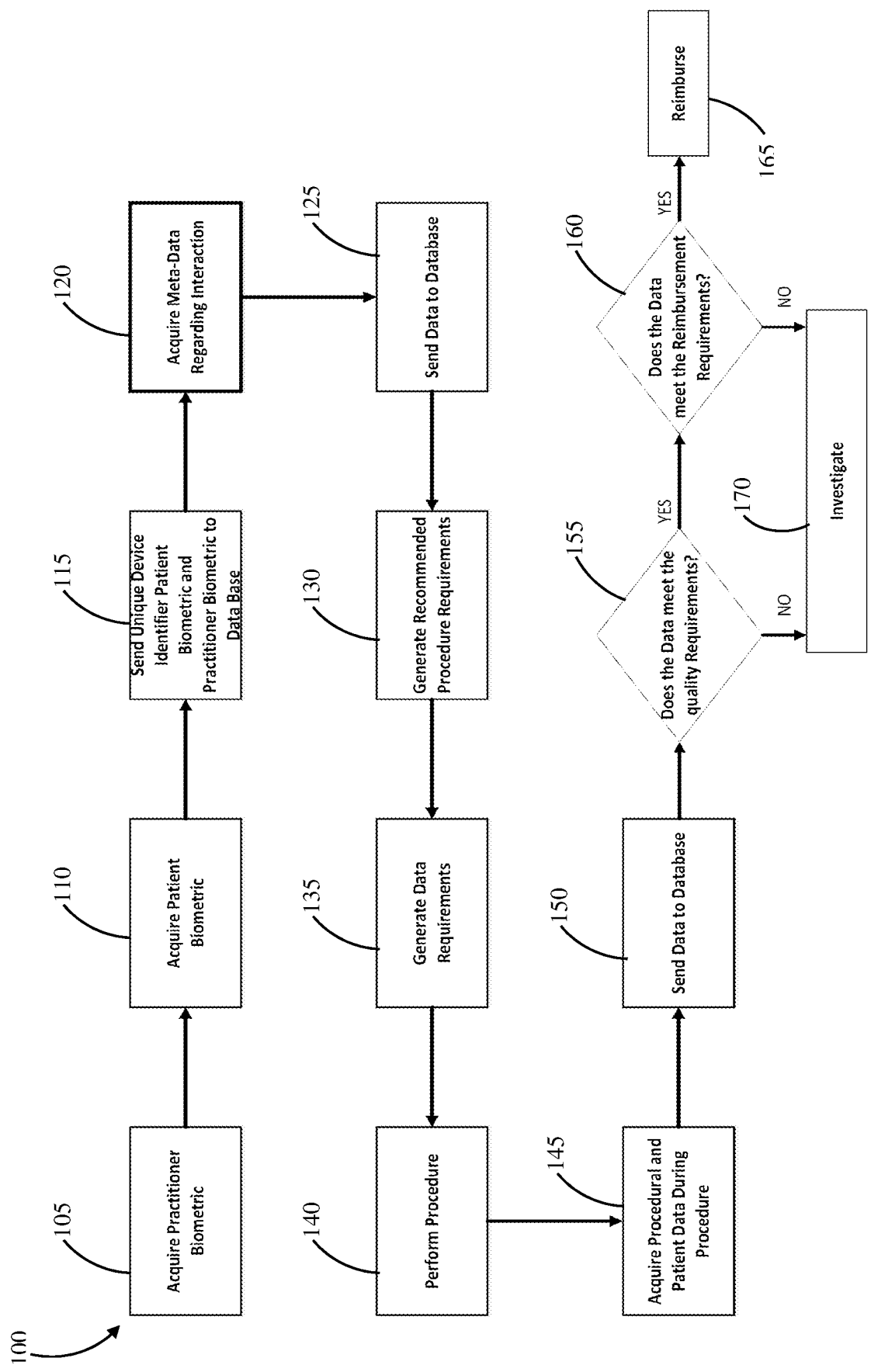
FIG. 1 illustrates an example workflow and data collection of an embodiment of the present invention.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

As used herein, the term "meta-data" refers to data that describes and gives information about other data, and the term "raw data" refers to data collected at a source without processing or other manipulation.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

The Healthcare Industry is being transformed through vertical integration of medical insurance Payers and medical Providers. This is driving the need for a health care system that facilitates the minimization of costs over the lifetime care of a patient as opposed to healthcare that is geared towards a single procedure to a patient.

Prior to this integration of Payers and Providers, it was in the practitioner's best interest (economically) to perform the costliest procedures and to perform more of them. In addition, fraudulent reimbursement claims become more frequent with practitioners splitting more of their time amongst multiple surgical procedures simultaneously and thus acting neglectfully towards patient care, all the while claiming reimbursement for the full procedure.

In contrast, after integration of Payers and Providers, it is in the best interest of the practitioner and payer to reduce healthcare costs over the lifetime of the patient. Thus after integration, the coupled Payer and Provider entity have interests aligned towards maximization of profit through minimization of costs. This introduces, for example, new interests in preventative healthcare and determining which procedures work for which diagnoses.

This example of preventative healthcare and determining most effective procedures highlights the need for an analytics based system of reimbursement. An analytics based system of reimbursement may be used to minimize lifetime patient healthcare costs through better correlation of treatment options with patient recovery, better measures of a practitioners' value and optimization of reimbursement pricing, built atop a foundation of common metrics derived from quality data. The problem lies in enforcing quality standards and processes to enable an analytics system that can meet the needs above.

A solution to this problem provides for a system level integration of a healthcare database and healthcare reimbursement cycle into a new framework wherein both data quality and data acquisition procedures are enforced and allow for intra-patient and inter-patient comparisons of data.

The System Breakdown

The following system breakdown describes elements of a data-centric patient care continuum (including examples). The data-centric patient care continuum may be used to acquire sufficient non-variant data (including digital/DICOM data) to enable a healthcare analytics capacity and thereby facilitate newly erected payer-provider healthcare entity models. In particular, the newly erected payer-provided healthcare entity models may use the healthcare analytics enabled via the data-centric patient care continuum to determine optimal treatment strategies and reimbursement.

The Framework

The present invention provides a computerized system and methods for generating and processing an integrated workflow to support the provision and reimbursement of healthcare services. In contrast to current electronic medical record systems, which are text-based, the present invention integrates digital, DICOM and video based data. In some embodiments a differentiator between text-based and source imaging data as included in the system described, is the reliance on summarization when providing text-based data. For example, when annotating the completion of a procedure post-surgery as part of a reimbursement report practitioners may begin to summarize the same surgical procedure via the common steps performed and leave out vital information such as the nuances of each procedure with respect to the others. This may result in non-descriptive and non-differentiable reports that omit vital information, mainly the elements that differentiate one surgical procedure performed on a patient from the same surgical procedure performed on another patient. To illustrate, take a doctor that performs a Tumor Resection surgery on a deep seated tumor. A very high level overview of the surgery would have the steps of draping the patient, registering the patient, performing the craniotomy, advancing to the tumor, resecting the tumor, retracting out of the patient, and closing the wound. Now these steps can be used to describe both the surgical procedures that were performed on both patients on a reimbursement report. Although these steps are sufficient, they lack any descriptive data that could be used to differentiate between the outcomes of the patients. For example, if three main vessels were traversed to reach the tumor in the first patient and only one were traversed to reach the tumor in the second patient, and the second patient had more complications post-surgery, the information regarding the number of vessels traversed would be omitted given the text-based data recorded regarding the surgery. On the other hand, if the report included imaging that contained the surgeon's chosen trajectory and the vessels crossed, then the increase in complications could be linked to the patient with the more vessels traversed. In this way providing imaging in the form of raw-data to the data continuum may be in some embodiments more valuable and useful than simply providing annotated text or in the best case of EMR static images with annotations. To clarify, static in this context implies screenshot type images as opposed to interactive imaging such as a 3D plan that may be interrogated as post-procedure. To further clarify, the example given between a static image and a 3D plan should not be taken to limit the system as described herein or the data the system may capture and employ.

Referring to the figures generally, and initially to FIG. 1 in particular, an exemplary computing system environment, for instance a medical information computing system on which the present invention may be implemented, is illustrated and designated generally as reference number 100. It will be understood and appreciated by those of ordinary skill in the art that the illustrated medical information computing system 100 is merely an example of one suitable computing environment and is not intended to suggest any limitation as to the scope of use or functionality of the invention.

Referring to FIG. 1, an example workflow and data collection for an analytics-based system of reimbursement for a health care event is illustrated. An interaction between a practitioner and a patient, also referred to here as a health care event, requires the collection of data relating to "who", "where", "when" and "why". The "who" refers to the practitioner and the patient and is fulfilled by acquiring a unique practitioner identifier including a biometric 105, and a unique patient identifier including a biometric 110. This information is sent to a database 115. The "where" and "when" for the health care event may also be acquired, using a unique identifier for the location of the interaction and a time stamp which can be included in the metric of the practitioner and patient identifiers. The "why" for the health care event is also acquired, which is the reason for the interaction. Together, the who, where, when and why comprise the meta-data 120 for the health care event and provide the context of the interaction however, this again should not be taken to limit the scope of what meta-data may include and is given as an example only. This meta-data serve as truth data that confirms the identity of all parties and devices. The meta-data is sent to a database 125 and used to generate recommended procedure requirements 130 and data requirements 135. The procedure is then performed 140, making up the "what" of the interaction, and procedural and patient data is acquired 145, making up the "how" of the interaction. Importantly, the "how" is achieved using a device and is associated with metrics from the device. The data from the device is provided directly, rather than through a text-based interpretation of digital data, thus it is a "truth-source" of quality assured data some embodiments of which are described in further detail above. The procedural and patient data (the "what" and "how") make up the "raw data" however, this again should not be taken to limit the scope of what "raw-data" may include and is given as an example only, and is sent to a database 150. The meta-data and raw data is analyzed to determine, first, whether it meets the quality requirements 155, and if so whether it meets the reimbursement requirements 160. If the data meets the quality requirements 155 and the reimbursement requirements 160, a reimbursement is calculated 165. If the data does not meet the quality requirements and/or does not meet the reimbursement requirements, the reimbursement claim is investigated 170. In this system, an individual not trained in the art can verify the procedure to have been completed correctly, that is, it is non-technical person verifiable. This may be seen as beneficial from the payer perspective in that in some instances it reduces the skill level needed of individuals reviewing the data resulting in reduced employment costs and a greater supply of individuals that may perform the reviewing task.

In this analytics-based system, a quality metric is associated with every measurement and every piece of data comes with an electronic signature so that the quality of the information is verifiable. The electronic signature of the practitioner is a two-factor authentication including a biometric, rather than, for example, a number based identifier that can be shared among medical personnel. Having a two-step authentication in which one is a biometric resolves this issue of fraudulent number sharing. The patient biometric also provides safety to verify the data corresponds to the correct patient. In some instances the quality of the information that is acquired may be dictated (upon input into the system) by a verification chip. This verification chip (physical, software, or otherwise) may act as entry gate to the data-highway and in addition assure that any data entering the data highway has a quality level associated with it. The quality level of the data may be based on various parameters such as the device used to acquire the data, the software setting of the data that was acquired or other applicable parameters. In general the quality level may in some instances reflect the confidence that the data quality was acquired in the correct manner adherent with best practices as predefined in the system or in other instances may reflect the quality of the device used. For example when entering an MRI image into the data-highway the age and make of the MRI System may be used to add a quality metric to the data, where older more less refined Systems would have a lower quality metric than newer more advanced ones. In another example the quality metric may dynamically change given the number of scans taken before the machine if recalibrated using a calibration phantom for example. This may be applied by reducing the quality metric level every ten scans until the machine is recalibrated whence the machine would again return to its highest quality level. In yet another examples the quality of the machine may be based upon a calibration system reading where a phantom with a known scan image may be compared to a scan taken with the machine and a comparison between the known scan and taken scan may be used to determine the level of accuracy attainable by the MRI machine and consequently a quality metric for a similar or identical scan taken of a patient with the same machine. It should be noted that although the quality metric examples provided here are given for MRI other imaging modalities may also be integrated with a verification chip to assign quality to their scans in a similar way such as CT scanners, PET scanners, and etc. More over the V-chip may also be applied to other medical devices such as navigation systems, robotic surgical systems, spectroscopy systems and etc. where the quality metric may eb associated with attributes of those machines. To further elaborate a robotic arm for example, may have a quality metric based on its accuracy in a positioning an end effector at a position as measured compared to a CCMs output in performing attaining the same positioning. To elaborate yet further a spectroscopy system may have a quality metric determined by its Signal to Noise Ratio.

Continuing with the example of inputting data into the continuum, a break in the availability of quality data implies a break in data continuum and the presence of "breaks" can imply an attempt at fraudulent healthcare claims. For example, magnetic resonance scans at a local hospital facility which is trusted by the insurance provider will have a high quality value to reflect the fact that measurements can be trusted. Magnetic resonance scans done at another facility for a short period will have a lower trustworthiness, hence the correlation metric will be correspondingly lower.

In addition to reimbursement, the data can be used for subsequent actions. The quality metric or quality assurance score of the data in this instance would speak to the reliability of the data input for subsequent actions and for learning what the most effective procedures for a given medical condition are. Using the quality data derived directly from the medical procedure, rather than textual-based data that is abstract and has a high variance, can also play a key role in establishing what constitutes a priori agreed procedures for specific medical conditions and enrolment of those procedures. A significant amount of pre-procedure testing is typically carried out, which is quite cumbersome and labour intensive. Using quality data to determine a priori agreed procedures will assist in workflow and reduce cost by eliminating the need for much of the pre-procedure testing. In the current systems, approval is needed to do a procedure, such as a scan, but as quality data is developed and a priori agreed procedures are established, an automatic pre-approval process can be implemented. This may be highly beneficial to both payors and especially providers, as providers may be reimbursed much faster which frees up monetary resources to be allocated to other needs in a hospital system. In addition this may also reveal issues with practitioners performing in line with best-practices as determined by the payer much faster than if the practitioner had to wait a month to get the feedback from their reimbursement claim not going through.

Figure 2:
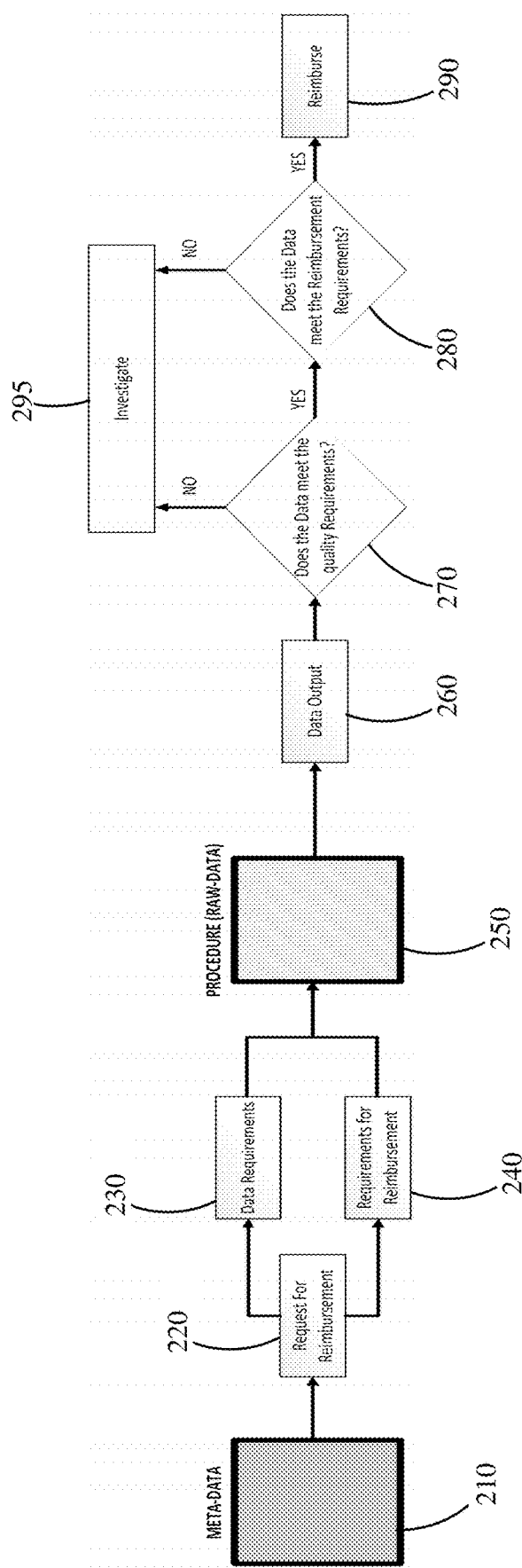
FIG. 2 illustrates a schematic of the workflow a practitioner may use to receive reimbursement.

Referring to FIG. 2, a flow diagram of an embodiment is provided illustrating the steps a practitioner will go through to be reimbursed by a payer. The first step 210 requires the practitioner to provide the meta-data of the interaction. As described above this defines the context of the interaction. Specifically it describes the reason for the patient being there, the patient, the practitioner, location of the interaction and time. Once this information is input into the data-highway/system by a request for reimbursement 220, the data-highway/system will determine what procedure or procedures the practitioner may prescribe and provide two checklists (or one amalgamated one) containing requirements that the practitioner must meet regarding the procedure they intend to perform on the patient in order to be reimbursed. The first checklist "Data Requirements" 230 will contain specific types of data that need to be captured during the practitioner performing the procedure as well as the quality of that data. As is apparent from the description this checklist will allow the payer to enforce a high level of data quality and data acquisition procedures. The second checklist "Reimbursement Requirements" 240 describes to the practitioner certain metrics they must acquire to be eligible for the reimbursement. These metrics, unlike the "Data Requirements" metrics, are specifically aimed at the state of the patient before, during and after the procedure. In this way the payer is able to monitor the health of the practitioner's patients and truly determine the practitioner's value. This also enables the system to determine if treatments are effective in that if the before and after metrics don't change for the better, then the treatment may be ineffective and cost inefficient. Thus, an iterative process is provided, wherein a procedure is chosen and followed, patient data are collected, the data is analyzed to determine the effectiveness of the procedure, and subsequently the recommended procedure and expected outcomes can be adjusted according to the collected and analyzed reimbursement data.

Continuing with the flow chart, once the requirements are provided the next step for the practitioner is to perform the procedure 250 and acquire and store the required data 260. Pre- and post-operative imaging data may be collected as part of the Data Requirements metrics. The pre- and post-operative imaging data may be used for quality assurance to confirm that an intended procedure was indeed performed.

This data is then checked for consistency with the quality requirements 270 and the reimbursement requirements 280. If the requirements are met the practitioner is payed 290, otherwise the practitioner is investigated 295.

Figure 3:
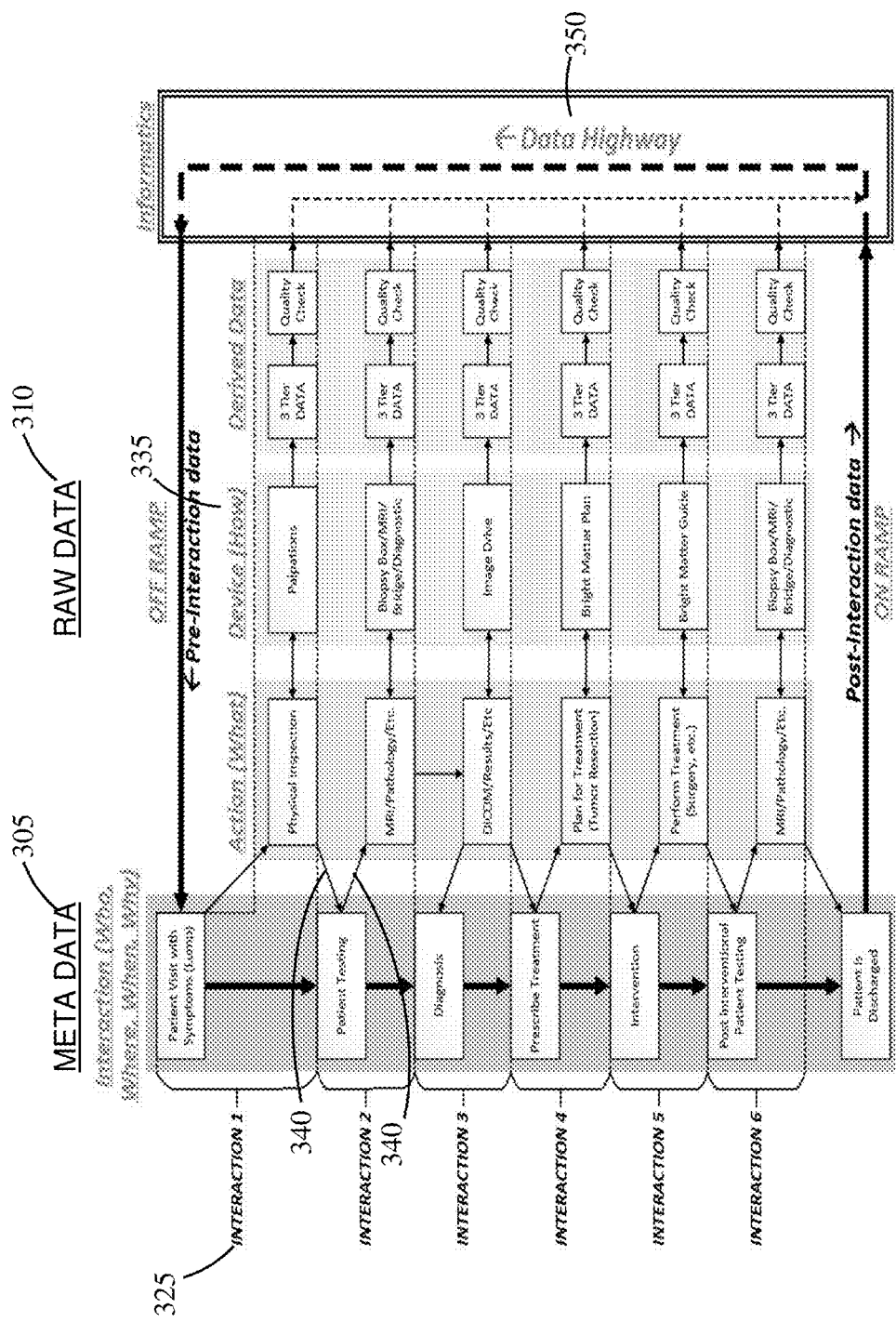
FIG. 3 illustrates a framework of an embodiment of the present invention.

Referring to FIG. 3, a flow diagram is provided of data through a Healthcare database system broken down into stages showing at what stages the meta-data 305 and raw-data 310 of the interactions are acquired.

The system works on the premise that any time patient healthcare data is accessed the event is recorded 315, inclusive of at minimum, who accessed the data and when it was accessed. This creates a "Data Highway Continuum" 320, which is essentially a record of every health related event the patient has had. These records are comprised of meta-data 305 and raw-data 310 which describe the context of the event and the event itself respectively. In contrast to current electronic medical record systems, the meta-data 305 and raw-data 310 are authenticated and digital/DICOM-based, rather than text-based, and thus provide a true account of the health care events.

A second premise of the system is that each interaction (event) 325 involves the practitioner acting on the patient in the form of a "procedure" whether this be a general inquiry, testing of the patient, or treating the patient 330.

A third premise is that the practitioner will seek to be reimbursed for each event.

A fourth premise is that data will be used for learning and predictive analytics to guide care of other patients with similar conditions.

The following description of the system works on the principle that each interaction 325 between the patient and the practitioner, also referred to as a health care event, may be described quantitatively (including character strings) with respect to the following questions, as described above. The first four questions address the who, when, where, and why 315 and provide the meta-data 305 of the interaction. The fifth and sixth questions address the what 330 and how 335 and provide the raw-data 310 of the interaction. To elaborate further the meta-data 305 of any interaction 325 may be used as a key to link 340 the raw-data 310 of the respective interaction to other similar interactions.

The descriptive framework is provided as follows:
1. Who: Who is present at the interaction: Who is the practitioner? and who is the patient?
2. Where: where does this interaction occur? (can be acquired by location stamping)
3. When: when does this interaction occur? (can be acquired by time stamping)
4. Why. The reason for the interaction and or procedure
5. What: The procedure being applied to the patient (as determined by the practitioner)

6. How. How and with what devices (if any) was the procedure performed (as performed by the practitioner)

The first requirement for this embodiment of the system is that each interaction 325 between a patient and a practitioner will require the practitioner to access the patient medical file. This in turn will create a health care event that will be recorded in the continuum along with any subsequent information regarding the event. In order to gain access to the patient file, at minimum three elements will be required. These elements will ideally be acquired asynchronously during the interaction and will reveal the meta-data 305 of the who, when, and where 315 of the interaction. More specifically, the elements required at the interaction are:

1. Unique identifier of the practitioner and time of identification
2. The unique identifier of the patient and time of identification
3. If a specific device is being used to measure the location, the unique identifier of the device and time of identification The unique identifier should include a biometric to exclude abuse of identifiers such as numbers that may be shared for fraudulent claims.

Once the who, when, and where of the interaction are acquired the next step is to determine the why 315 of the interaction. The why must be inputted into the system manually as meta-data 305 by the practitioner or in some cases asynchronously as meta-data derived from the device being used. This meta-data 305 provides a description of the reason for the interaction. The why 315 of the interaction describes why the patient is having the interaction with the practitioner. Three main examples include the patient is getting a check-up, the patient has symptoms, or a previous diagnosis that the patient requires treatment for. There are generally two encompassing types of interactions that may occur given the three previous examples of why an interaction is needed:

1. Diagnostic interaction: for deciphering an ailment (including determining whether or not an ailment exists). Usually requiring a type of test, for example:
   a. primary care physician (PCP) regular checkups: PCP inquiry/palpations/visual inspections of the patient
   b. Pre-surgical testing: imaging and biopsy, molecular profile of biopsy
   c. Post-surgical checkup: MRI scan, etc.
2. Treatment interaction: for treating the ailment (given one is present). In this case the why is predetermined by the diagnostic procedure (prior event) leading up to the treatment procedure.
   a. Prescribing prescription drugs
   b. Performing surgery
   c. Radiation therapy
   d. Other types of treatments Once the meta-data 305 of the who, when, where, and why are acquired the what 330 and how 335 of the procedure are needed as they provide the raw-data 310 of the interaction that may be analyzed in light of the context provided by the meta-data 305. The what 330 and the how 335 directly result from the practitioners' actions (raw-data 310) in addressing the why 315 of the interaction and may be used to hold the practitioner accountable for their choice of actions in regards to treating the patient.

The what 330 and how 335 of the procedure are illustrated as follows:

1. Diagnosis example:
   1. The given why. Checkup
      i. The what and how: palpations performed by the practitioner
      ii. The what and how: inquiries of the patient performed by the practitioner
   b. The given why. Complaint by patient of momentary blindness
      i. The what and how: MRI performed with device A
      ii. The what and how: Biopsy performed with device B
2. Treatment example:
   a. Given diagnosis (the why): Wart
      i. The what and how. Freezing Method using device A
      ii. The what and how. Pharmaceuticals A by oral ingestion by the patient
   b. Given diagnosis (the why): Glioblastoma (GBM)
      i. The what and how: Radiation Therapy using device A
      ii. The what and how: GBM Resection using device B To reiterate the information acquired by the system up to this point provides for the 1. who: provided by the patient and practitioner identifiers.
2. where: provided by the device used to access file
3. when: provided by the device used to access file
4. why: provided by the reason for the interaction
5. what: provided by the procedure performed,
6. how: provided with information as follows:
   a. With what device
   b. all recorded metrics associated with the patient
      i. heart rate,
      ii. video of patient,
      iii. intraoperative MRIs
      iv. anything related to patient biology
   c. all recorded metrics associated with the actions of the practitioner
      i. number of movements of drive
      ii. adjustments to trajectory
      iii. amount of anesthesia
      iv. etc.

A significant link in this chain of interaction is that the motivation for performing the what 330 and the how 335 of the procedure can be traced back to the why in the meta-data 305. The why 315 provides the context of the interaction while the what 330 and the how 335 provide the actions taken by the practitioner as well as the state of the patient throughout the interaction.

Importantly, the meta-data 305 and raw data 310 is sourced from a "truth source" and maintained as immutable data. For example, data for how 335, such as DICOM or digital information, is captured contemporaneously in the background from a medical device used in treatment, for example MRI parameters and an MRI image. Thus streams of digital data are collected in real-time, unlike current electronic medical records, which are textual-based systems where the data is described and captured post-surgery. This data capture in real time from the medical device frees the practitioner from having to capture the data and prevents the data from omitting important nuances that could effect be used for analytics purposes to improve best-practices. The practitioner is able to annotate during the procedure, for example in a video stream the practitioner may dictate (i.e., "inserting pedicle screw in 04"), which is captured with the video stream. In particular, those components that have clinical or billing relevance may be annotated. This system therefore does not rely on textual abstracting of the data by the practitioner. Textual abstracting can drive individuals to template the results and cut and paste the information, a dangerous practice because the summarizations do not capture the uniqueness of the report, so information may be left out.

Another aspect of this framework is that the raw data 310 collected for each interaction 325, including interactions for multiple patients, can be anonymized, aggregated and analyzed to correlate which procedures are most effective for a given medical condition, both in the short and long term outcomes. The analysis of aggregated data may also be used to update the data quality requirements so that the procedure is carried out in the most effective way. Thus a data highway 350 is provided which continuously accumulates information and is owned by the payer.

The accumulated information may be used to evaluate and improve the choice of procedure for a given patient presentation, using an iterative learning process as more data is collected. The accumulated information is analyzed statistically to correlate a given "why" (the reason for the health care event), a subsequent "what" (the treatment) and "how" (the device and metrics), and the patient outcome. Thus, with accumulated information, an a priori agreed upon procedure is provided to the practitioner for a given medical condition, based on prior health care events and outcomes. This can provide a huge time saving in medical care, because variance is reduced: when a patient presents with particular symptoms, the optimal procedure is determined and automatic approval for specific tests or treatments is provided, including specific components to be performed.

Another feature of the framework is that subsequent interactions can be generated by adding new data to existing data, and thereby generate a second interaction or health care event. However, in generating the second interaction the data from the first interaction cannot be changed, including the digital signatures associated with the first interaction. This may be achieved by associating digital signatures with each version of the data. Any new version inherits existing parameters of the data in an immutable fashion and then adds more data, including another signature.

Figure 4:
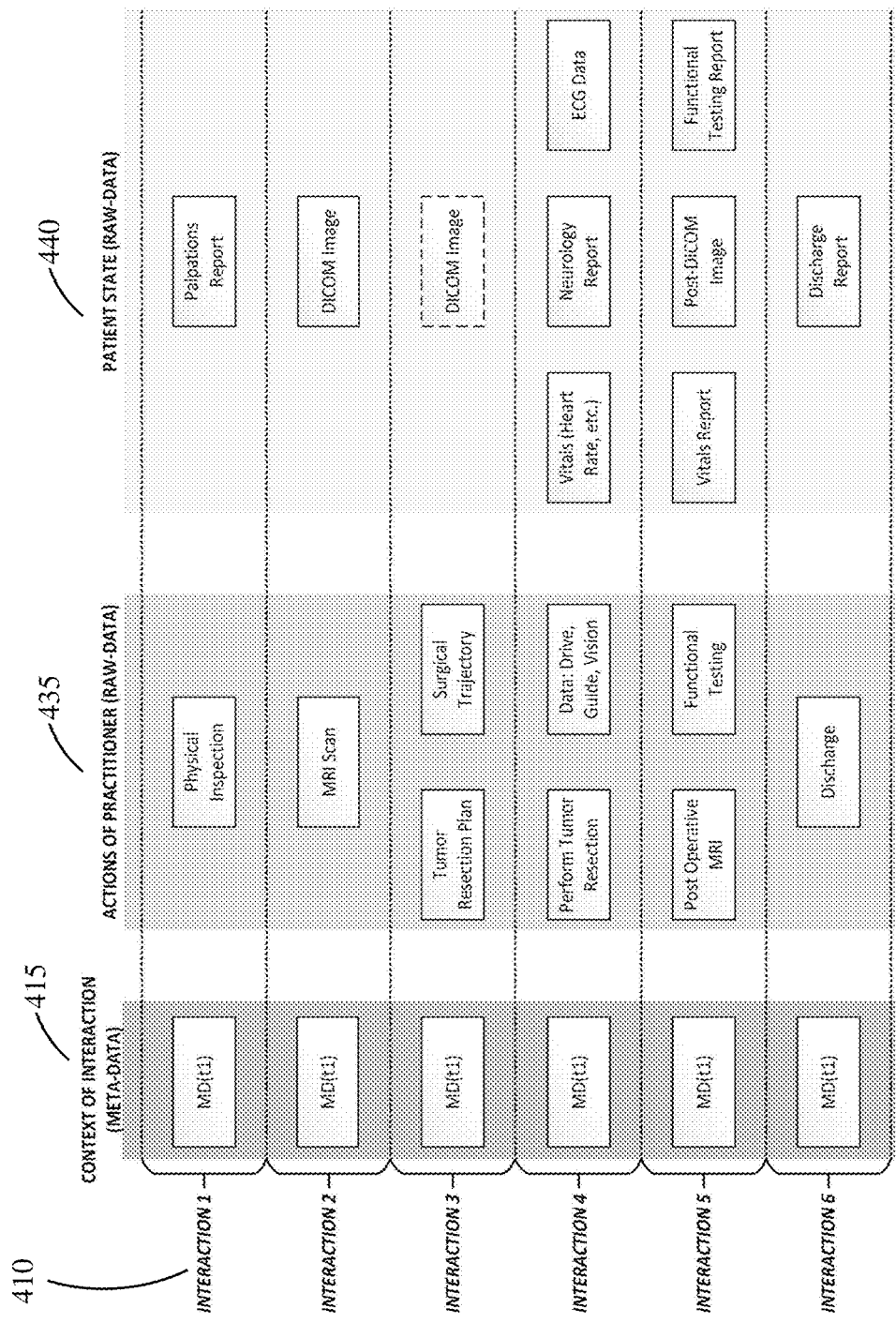
FIG. 4 illustrates three tier data acquisition with a framework of an alternate embodiment of the present invention.

Referring to FIG. 4, an alternate three-tier data acquisition framework is illustrated. At left, each patient/practitioner interaction 410 has associated meta-data 415. The raw data associated with the actions of the practitioner 435 for the procedure includes metrics provided by a device or devices used in the procedure. The raw data also includes the patient state 440, and includes analytical device measurements such as DICOM images from MRI scan, vitals, ECG data, etc.

Figure 5:
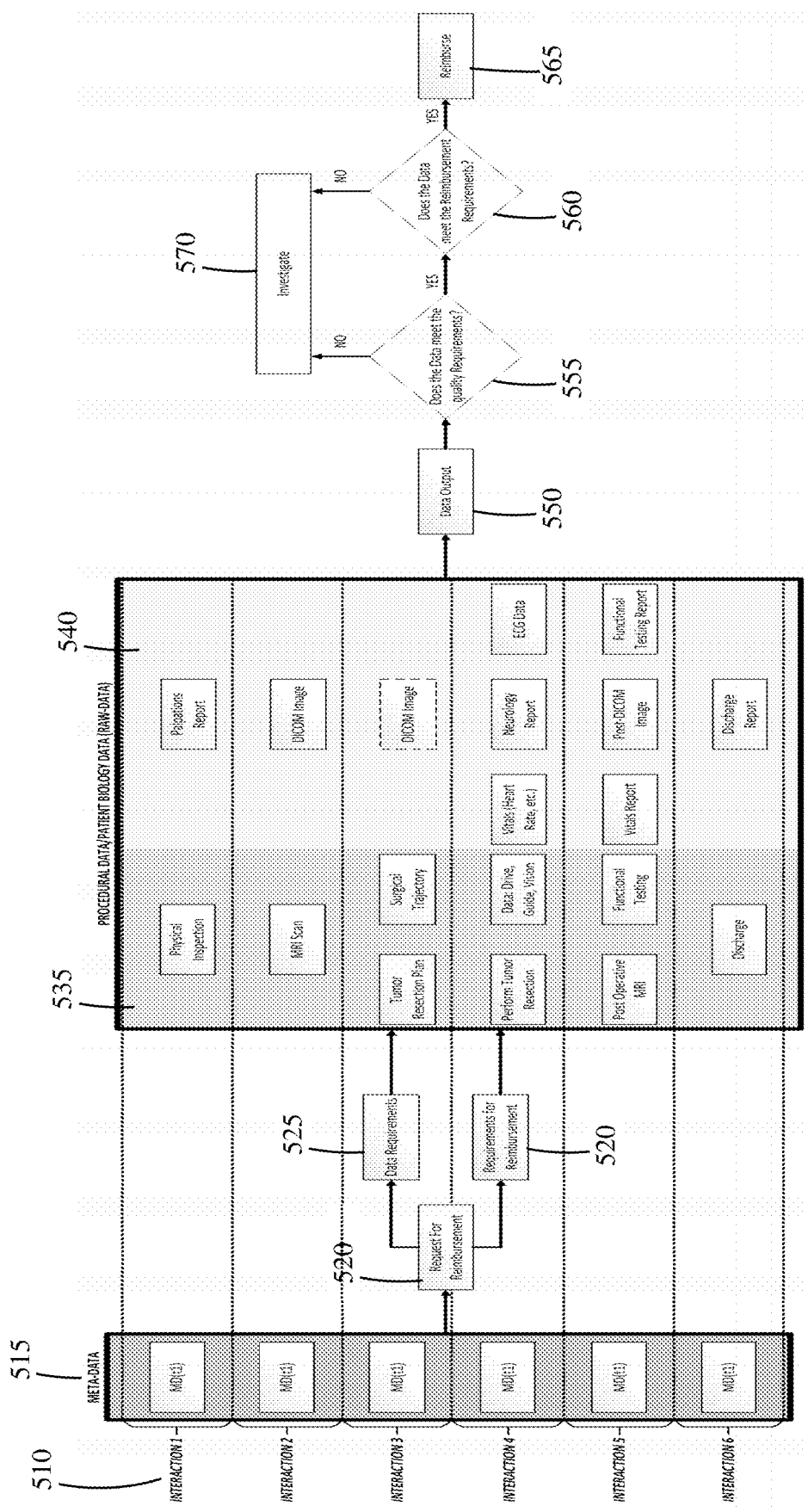
FIG. 5 illustrates entry points to data acquisition with a framework of an embodiment of the present invention.

Referring to FIG. 5, the three-tier data acquisition framework is shown in context of the reimbursement flow chart provided in FIG. 2. Each health care event or interaction 510 is associated with meta-data 515. Data acquisition occurs when the meta-data 515 is accessed by the practitioner and a request for reimbursement 520 is submitted with the meta-data. Consequently a list of data requirements 525 and requirements for reimbursement 530 for the procedure is generated. Raw data from the procedure 535 and patient biology 540 are output to a database 550. The acquired data are then analyzed to determine if the data meets the quality requirements 555 and the reimbursement requirements 560 The quality requirements 555 may be automatically managed by the devices acquiring the data. If the data meets the quality requirements and the reimbursement requirements, the practitioner is reimbursed 565. If the data requirements are not met, the practitioner is investigated 570.

Figure 6:
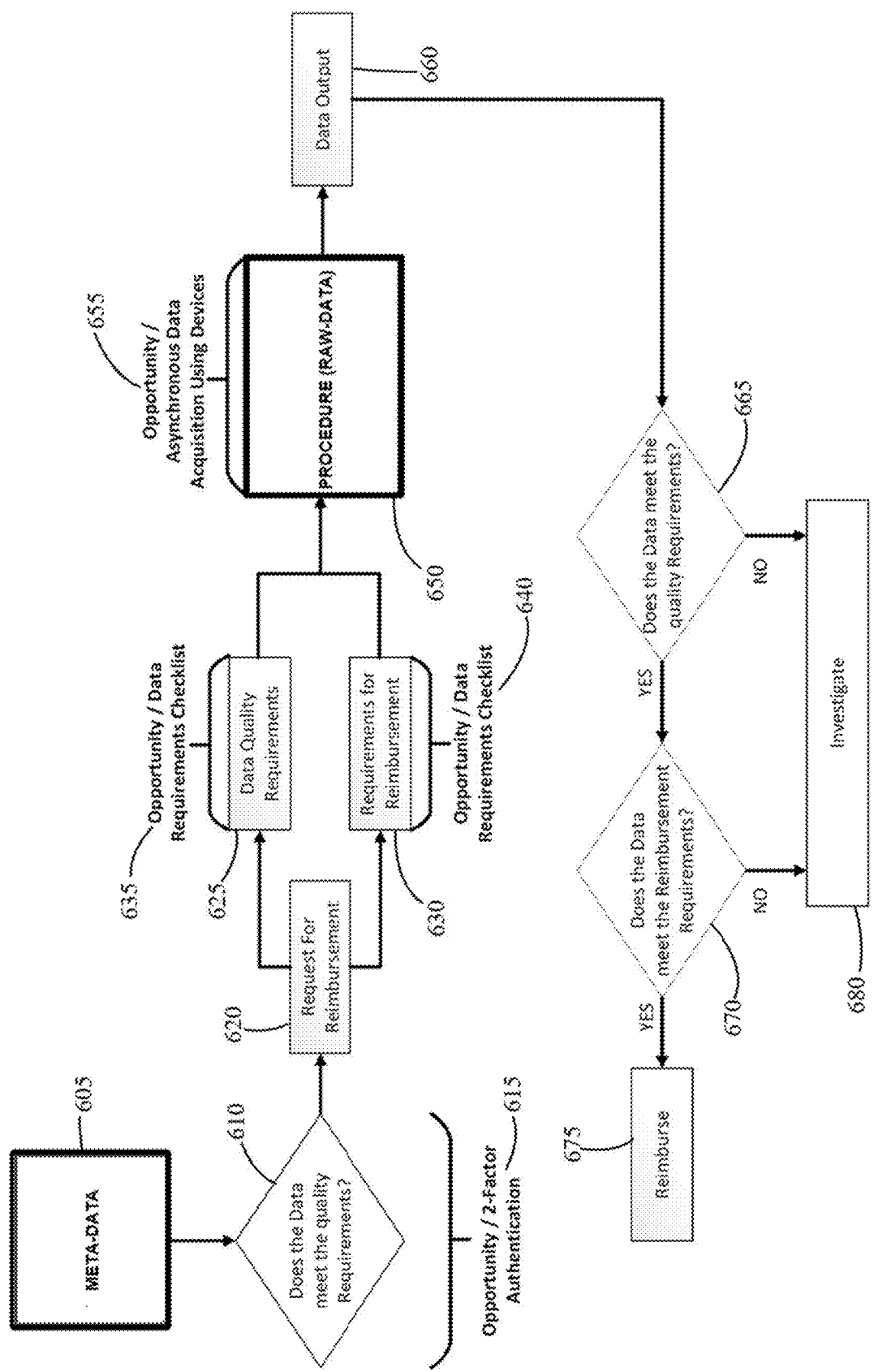
FIG. 6 illustrates a work-flow schematic of the current invention.

Referring to FIG. 6, an example of workflow for an embodiment of the present invention is shown. A patient/practitioner interaction or health care event provides meta-data 605, including a unique patient identifier, a unique practitioner identifier, a health care site identifier which can be provided by a location device, the time which can also be provided by a time stamp associated with each of the patient, practitioner, and location identifiers; and the reason for the health care event. The meta-data is analyzed to determine whether the data meets the quality requirements 610. This data check provides an opportunity to require quality data for the contextual information regarding the health care event. For example, the unique practitioner and patient identifier requires a two-factor authentication. The two-factor authentication may require a biometric and device such as a wristband. Another method is to provide each practitioner with their own authentication key that has a public and private key component. The key is issued by a key issuing authority, namely the insurance company. The insurance company would provide the keys to hospital systems and their staff. When data is watermarked using these issued keys, the insurance company knows that the data was generated by an individual who is "trusted" by the insurance company. Alternatively, the identification and authentication may employ blockchain technology. By combining the decentralized blockchain principle with identity verification, a secure digital ID can be created for the practitioner which can be assigned to every transaction. Employing blockchain for authentication would allow a check of the identity on every transaction in real time, thus reducing or eliminating the rate of fraud.

After checking the meta-data for quality requirements, a request for reimbursement 620 is generated and data quality requirements 625 and requirements for reimbursement 630 are provided. This provides another opportunity for requiring data quality 635/640, in that a data requirements checklist is provided with the procedure, thus the practitioner can review the criteria and employ the most effective and efficient methodology. It also provides an opportunity for the payer to require a standard of care in order for reimbursement to occur, and the standard of care can be measured analytically using the provided data quality requirements 625 and requirements for reimbursement 635.

The procedure is then carried out 650 and raw data 655 is collected using one or more devices required by the procedure. This step also provides an opportunity for ensuring data quality, because the raw data is derived from measurements acquired by devices used in the procedure. In the current invention, for the raw data there is no abstracting of information, only annotation of the "truth source" (i.e. DICOM, digital, video-based data), so the actual event with every nuance is captured unaltered. The raw data is output 660 and can be compared to the data requirements 625, 630 to quantify reimbursement 675 according to how close the data matches the quality requirements 665 and whether the data meets the reimbursement requirements 670.

This system allows more efficient and rapid reimbursement claims, since the data requirements are provided with the elected procedure and data is collected in real-time directly from the devices used in the procedure, thus freeing the practitioner from abstracting the data textually. The procedure list provided by the system includes a priori approved procedures, thus approval requests and permission for specific tests included in the procedure can be automated. As well, the information is verifiable by a random third party who is, for example, employed by the payer insurance company.

Referring to FIG. 7, an example of a data requirements checklist is illustrated for a procedure, specifically a resection. The procedure utilizes several medical devices for resection, navigation, pre-operative and intraoperative imaging, and to monitor vital signs. As the procedure is underway, the devices used provide metrics to populate the requirements checklist. These metrics may be used to determine if reimbursement should be provided and whether full or partial reimbursement should be provided. By populating the checklist with data from the medical devices, the practitioner is freed from providing the data textually, and the data is quality assured. The data can later be aggregated and analyzed with other patient data from the same or comparable procedures in order to assess the optimal parameters and effectiveness of the procedure.

Further embodiments of the current invention are provided here.

EXAMPLE 1

Tumor resection requires an MRI prior to resection in order to visualize the tumor site and size. When practitioners evaluate each patient for a tumor in a given region, it is a laborious and time-consuming process requiring a request and an approval process. By collecting quality assured data and analyzing it in an iterative learning process, a standard procedure is established, so that the request and approval process can be integral to the procedure and the process is streamlined. By streamlining the process, money and time is saved and the procedure is standardized.

EXAMPLE 2

In diagnosing a patient that is losing vision, a visual field is determined showing the impairment. Consequently, an MRI is requested and approved, and the MRI reveals a lesion that requires surgical intervention. Following the surgery, a follow-up determination of visual field and an MRI is included in the standard procedure. The data from the medical devices (i.e. "truth sources" including direct data from optical instruments, MRI, surgical navigation system, video of surgery) is captured contemporaneously, with the data being immutable. The captured data confirms the procedures authorized pre-operatively were completed and the post-operative data confirms that the procedures were effective. The data also confirms that reimbursement can be made. The post-operative visual field of the patient and MRI data provide feedback on the interventions that were agreed upon. The quality assurance datasets that were included in the procedure create an iterative learning experience that drives treatment algorithms, and closes the loop by determining the optimal procedures to follow. When a subsequent patient presents with the visual impairment, the system automatically triggers a visual field be obtained and automatically pre-approves the rest of the algorithm if they stay on the algorithm.

EXAMPLE 3

A cancer patient has a tumor removed, and the tumor biopsy is used for histological analysis and molecular analysis by polymerase chain reaction (PCR). The patient is treated with a chemotherapy regime and the effectiveness of the chemotherapy is correlated with the tumor biopsy data. By an iterative learning process, the most effective chemotherapy for a tumor with that molecular fingerprint is determined and thereafter provided in the procedure recommended by the system.

EXAMPLE 4

With current systems, when a radiologist interacts with a digital read, an abstract archive is created in a radiology report. Instead, in the current invention that radiologist interaction can be captured (i.e. screensaver, video, voice dictation, similar to the live annotations for surgical procedures in Example 2 above), time-stamped and validated, thereby eliminating the abstract data. In this example, ImageDrive captures source imaging and captures the radiologist written report abstract analysis. Thus the image is quality assured data and can include a screenshot of the radiologist reading the report and include his annotations, instead of the abstract data provided by the radiology report.

In the examples above, the iterative learning can lead to new treatment paradigms (i.e., chemotherapy, tumor marker, approve chemotherapy treatment, provide validity of treatment protocol). In addition, because the system uses quality assured data, the number of data required may be reduced, because the current methods for electronic medical records have more variance due to abstract textual data, and thus more noise. With the quality assured data, fewer interactions may be required to impact the treatment paradigms because the data is quality assured and has less background variance/noise in the system.

The specific embodiments described above have been provided by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A computer-implemented method for recording a first health care event and calculating a reimbursement, the method comprising:
acquiring metadata for the first health care event in a memory of a medical device, the metadata comprising:
a patient identifier;
a patient identifier entry time;
a practitioner identifier;
a practitioner identifier entry time;
a health care site identifier;
a health care site identifier entry time; and
a medical reason for the health care event;
sending the metadata from the medical device to a centralized computer server;
receiving a request for reimbursement in the centralized computer server from the medical device;
generating a list of procedures based on the medical reason by the centralized computer server;
selecting a procedure from the list of procedures by the medical device;
generating a list of required raw data types for the procedure by the centralized computer server;
generating a list of required quality data for the procedure by the centralized computer server;
acquiring raw data for the first health care event by the medical device, the raw data comprising:
data acquired during the procedure by the medical device;

a medical device identifier;
a medical device identifier entry time;
one or more quality data from the medical device for the procedure, the one or more quality data comprising:
a number of scans the medical device has performed since the last calibration;
a resolution of the medical device; or
a signal to noise ratio; and
a patient status before and after the procedure;
sending the raw data from the medical device to the centralized computer server; and
calculating a reimbursement for the first health care event by the centralized computer server based on at least:
the procedure;
the medical device identifier;
the list of required raw data types for the procedure;
the list of required quality data from the medical device;
the data acquired during the procedure from the medical device; and
the one or more quality data from the medical device;
wherein the metadata and the raw data comprise two factor authenticated data; and
further wherein at least one factor of the two factor authentication is a watermark, an insurer-provided key, a biometric, a verification chip, a blockchain technology, or a public key.

2. A computer-implemented method for recording a first health care event and calculating a reimbursement, the method comprising:
acquiring metadata for the first health care event in a memory of a medical device, the metadata comprising:
a patient identifier;
a patient identifier entry time;
a practitioner identifier;
a practitioner identifier entry time;
a health care site identifier;
a health care site identifier entry time; and
a medical reason for the event;
sending the metadata from the medical device to a centralized computer server;
receiving a request for reimbursement in the centralized computer server from the medical device;
generating a list of one or more procedures based on the medical reason by the centralized computer server;
generating a list of required raw data types and a list of required quality data for each of the one or more procedures by the centralized computer;
acquiring raw data for the first health care event by the medical device, the raw data comprising:
a procedure selected from the list of procedures;
data acquired during the procedure by the medical device;
a medical device identifier;
a medical device identifier entry time;
one or more quality data from the medical device used in the procedure, the one or more quality data comprising:
a number of scans the medical device has performed since the last calibration;
a resolution of the medical device; or
a signal to noise ratio; and
a patient status before and after the procedure;
sending the raw data from the medical device to the centralized computer server; and
calculating a reimbursement for the first health care event by the centralized computer server based on at least:
the procedure;
the medical device identifier;
the list of required raw data types for the procedure;
the list of required quality data from the medical device;
the data acquired during the procedure from the medical device; and
the one or more quality data from the medical device;
wherein the metadata and the raw data comprise two factor authenticated data; and
further wherein at least one factor of the two factor authentication is a watermark, an insurer-provided key, a biometric, a verification chip, a blockchain technology, or a public key.

3. The method of claim 1, wherein the patient identifier, the practitioner identifier and the health care site identifier are retrievably stored in one or more databases.

4. The method of claim 1, wherein the patient identifier is anonymized.

5. The method of claim 1, further comprising:
generating a second health care event by adding additional metadata and additional raw data to the first health care event metadata and the first health care event raw data,
wherein the first health care event is immutable and the second health care event is associated with a second practitioner identifier entry time.

6. The method of claim 1, wherein the raw data for the health care event is aggregated and analyzed to modify the list of procedures, the list of data types and the list of quality data.

7. The method of claim 1, wherein
the procedure selected from the list of procedures is to record a radiology reading,
the procedure comprising:
providing a radiology image on a monitor;
viewing the radiology image by a radiologist;
capturing a screen-shot of the radiology image and a time-stamp of the viewing by the radiologist;
providing an annotation of the radiology image by an audio or video recording; and
storing the radiology image, the screen-shot, the time stamp and the annotation; and
the list of required data types comprises:
the radiology image;
the screen-shot of the radiology image with the time-stamp of the viewing by the radiologist; and
the annotation of the radiology image by an audio or video recording.

8. A health care data system to determine a reimbursement for a health care event comprising:
a medical device
for recording metadata for the health care event, the metadata comprising:
a patient identifier;
a practitioner identifier;
a health care site identifier;
a time entry for each of the patient identifier, the practitioner identifier and the health care site identifier; and
a medical reason for the health care event; and
for recording raw data for the health care event, the raw data including:
a list of procedures for the medical reason;
a procedure selected from the list of procedures;

a list of required raw data types for the procedure from the medical device;
　　a list of required quality data from the medical device for the procedure;
　　a medical device identifier;
　　a time entry for the medical device identifier;
　　data acquired during the procedure from the medical device; and
　　at least one quality data from the list of quality data, measured from the medical device for the health care event;
a central computer server in communication with the medical device, the central computer server providing the list of procedures, the list of required raw data types, and the list of required quality data to the medical device; and
a memory of the central computer server with an executable application for calculating the reimbursement quantum for the health care event based on at least:
　the procedure;
　the medical device identifier;
　the list of required raw data types from the medical device for the procedure;
　the list of required quality data from the medical device;
　the data acquired during the procedure from the medical device; and
　the at least one quality data from the medical device, comprising:
　　a number of scans the medical device has performed since the last calibration;
　　a resolution of the medical device; or
　　a signal to noise ratio;
　wherein the metadata and the raw data comprise two-factor authenticated data; and
　further wherein at least one factor of the two factor authentication is a watermark, an insurer-provided key, a biometric, a verification chip, a blockchain technology or a public key.

9. The health care data system of claim 8, wherein the quality data for the procedure includes a patient status before and after the procedure.

10. The health care data system of claim 8, wherein the patient identifier is anonymized.

11. The health care data system of claim 8, further comprising a processor and a memory with an executable application for aggregating the metadata and the raw data for analysis.

12. The health care data system of claim 11, wherein the executable application includes a correlation of the selected procedure with a patient status after the procedure.

13. The method of claim 2, wherein the raw data for the health care event is aggregated and analyzed to modify the list of procedures, the list of data types and the list of quality data.

* * * * *